United States Patent [19]

Chambers et al.

[11] Patent Number: 5,597,915

[45] Date of Patent: Jan. 28, 1997

[54] BENZODIAZEPINE DERIVATIVES, COMPOSITIONS CONTAINING THEM AND THEIR USE IN THERAPY

[75] Inventors: Mark S. Chambers, Watford; Stephen R. Fletcher, Hatfield Heath; Victor G. Matassa, Furneux Pelham, all of United Kingdom; Mark G. Bock, Hatfield, Pa.

[73] Assignee: Merck Sharp & Dohme Ltd., Hoddesdon, England

[21] Appl. No.: 295,918

[22] PCT Filed: Mar. 15, 1993

[86] PCT No.: PCT/GB93/00535

§ 371 Date: Sep. 15, 1994

§ 102(e) Date: Sep. 15, 1994

[87] PCT Pub. No.: WO93/19063

PCT Pub. Date: Sep. 30, 1993

[30] Foreign Application Priority Data

Mar. 16, 1992 [GB] United Kingdom ............ 9205669
Nov. 3, 1992 [GB] United Kingdom ............ 9223006

[51] Int. Cl.⁶ .......... C07D 417/12; C07D 413/12; C07D 403/12; A61K 31/55

[52] U.S. Cl. ............................................ 540/509

[58] Field of Search .................. 540/509; 514/215

[56] References Cited

FOREIGN PATENT DOCUMENTS

| | | |
|---|---|---|
| 0167919A3 | 1/1986 | European Pat. Off. . |
| 0434364A3 | 6/1991 | European Pat. Off. . |
| 0434360A1 | 6/1991 | European Pat. Off. . |
| 0434369A1 | 6/1991 | European Pat. Off. . |
| 0508796A1 | 10/1992 | European Pat. Off. . |
| 0508797A1 | 10/1992 | European Pat. Off. . |
| 514133 | 11/1992 | European Pat. Off. . |

OTHER PUBLICATIONS

Kawabata, Regulatory Peptides 35, 1–10 (1991).
Patel, *Molec. Pharm.* 46, 943 (1994).
Woodruff, Neuropeptides 19, (Suppl) pp. 45–46 (1991).
J. Med. Chem. 1989, vol. 32, pp. 13–16 by Mark G. Bock, et al., "Benzodiazepine Gastrin and Brain Cholecystokinin Receptor Ligands: L–365,260".

*Primary Examiner*—Mark L. Berch
*Attorney, Agent, or Firm*—Robert J. North; Melvin Winokur

[57] ABSTRACT

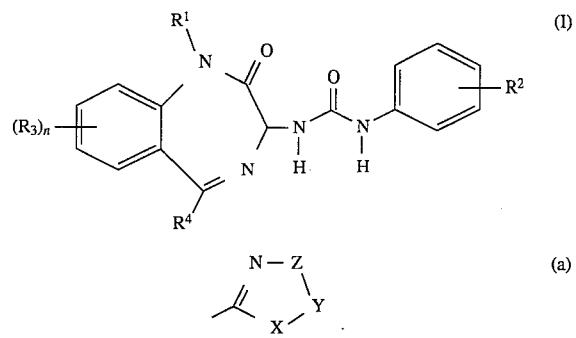

Compounds of Formula (I), and salts and prodrugs thereof wherein: $R^1$ is H, certain optionally substituted $C_{1-6}$alkyl or $C_{3-7}$cycloalkyl; $R^2$ represents a group (a) wherein X is O, S or $NR^8$ where $R^8$ is H or $C_{1-4}$alkyl; one of Z and Y is C=O and the other is O, S or $NR^9$, where $R^9$ is H or $C_{1-4}$alkyl; $R^3$ is $C_{1-6}$alkyl, halo or $NR^6R^7$; $R^4$ is $C_{3-10}$cycloalkyl; n is 0, 1, 2 or 3, and are CCK and/or gastrin antagonists, which compounds and compositions thereof are useful in therapy.

4 Claims, No Drawings

BENZODIAZEPINE DERIVATIVES, COMPOSITIONS CONTAINING THEM AND THEIR USE IN THERAPY

This application is a 35 U.S.C. §371 application of PCT/GB93/00535, filed Mar. 15, 1993.

This invention relates to benzodiazepine compounds which are useful as antagonists of cholecystokinin and gastrin receptors.

Cholecystokinins (CCK) and gastrin are structurally related peptides which exist in gastrointestinal tissue and in the central nervous system (see, V. Mutt, *Gastrointestinal Hormones*, G. B. J. Green, Ed., Raven Press, N.Y., p.169 and G. Nission, ibid. p.127).

Cholecystokinins include CCK-33, a neuropeptide of thirty-three amino acids in its originally isolated form (see, Mutt and Jorpes, *Biochem. J.* 125, 678 (1971)), its carboxy-lterminal octapeptide, CCK-8 (also a naturally-occurring neuropeptide and the minimum fully active sequence), and 39- and 12-amino acid forms. Gastrin occurs in 34-, 17- and 14-amino acid forms, with the minimum active sequence being the C-terminal tetrapeptide, Trp-Met-Asp-Phe-$NH_2$, which is the common structural element shared by both CCK and gastrin.

CCKs are believed to be physiological satiety hormones, thereby possibly playing an important role in appetite regulation (G. P. Smith, *Eating and Its Disorders*, A. J. Stunkard and E. Stellar, Eds, Raven Press, New York, 1984, p. 67), as well as stimulating colonic motility, gall bladder contraction, pancreatic enzyme secretion and inhibiting gastric emptying. They reportedly co-exist with dopamine in certain mid-brain neurons and thus may also play a role in the functioning of dopaminergic systems in the brain, in addition to serving as neurotransmitters in their own right (see A. J. Prange et al., "Peptides in the Central Nervous System" *Ann. Repts. Med. Chem.* 17, 31, 33 [1982] and references cited therein; J. A. Williams, *Biomed Res.* 3 107 [1982]; and J. E. Morley, *Life Sci.* 30, 479 [1982]).

The primary role of gastrin, on the other hand, appears to be stimulation of the secretion of water and electrolytes from the stomach and, as such, is involved in control of gastric acid and pepsin secretion. Other physiological effects of gastrin then include increased mucosal blood flow and increased antral motility. Rat studies have shown that gastrin has a positive trophic effect on the gastric mucosa, as evidenced by increased DNA, RNA and protein synthesis.

There are at least two subtypes of cholecystokinin receptors termed CCK-A and CCK-B (T. H. Moran et al., "Two brain cholecystokinin receptors: implications for behavioural actions", *Brain Res.*, 362, 175–79 [1986]). Both subtypes are found both in the periphery and in the central nervous system.

CCK and gastrin receptor antagonists have been disclosed for preventing and treating CCK-related and/or gastrin related disorders of the gastrointestinal (GI) and central nervous (CNS) systems of animals, especially mammals, and more especially those of humans. Just as there is some overlap in the biological activities of CCK and gastrin, antagonists also tend to have affinity for both CCK-B receptors and gastrin receptors. Other antagonists have activity at the CCK-A subtype.

Selective CCK antagonists are themselves useful in treating CCK-related disorders of appetite regulatory systems of animals as well as in potentiating and prolonging opiate-mediated analgesia [see P. L. Faris et al., *Science* 226, 1215 (1984)], thus having utility in the treatment of pain. CCK-B and CCK-A antagonists have also been shown to have a direct analgesic effect [M. F. O'Neill et al., *Brain Research*, 534 287 (1990)]. Selective CCK and gastrin antagonists are useful in the modulation of behaviour mediated by dopaminergic and serotonergic neuronal systems and thus have utility in the treatment of schizophrenia and depression (Rasmussen et. al., 1991, *Eur. J. Pharmacol.*, 209, 135–138; Woodruff et. al., 1991, *Neuropeptides*, 19, 45–46; Cervo et. al., 1988, *Eur. J. Pharmacol.*, 158, 53–59), as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value, see e.g. U.S. Pat. No. 4,820,834. Certain CCK antagonists are useful anxiolytic agents and can be used in the treatment of panic and anxiety disorders.

CCK has been reported to evoke the release of stress hormones such as adrenocorticotrophic hormone, β-endorphin, vasopressin and oxytocin, CCK may function as a mediator of responses to stress and as part of the arousal system. CCK-A receptors are now known to be present in a number of areas of the CNS and may be involved in modulating any of the above.

CCK may be involved in the regulation of stress and its relationship with drug abuse e.g. alleviation of the benzodiazepine withdrawal syndrome (Singh et. al., 1992, *Br. J. Pharmacol.*, 105, 8–10) and neuroadaptive processes.

Since CCK and gastrin also have trophic effects on certain tumours [K. Okyama, *Hokkaido J. Med. Sci.*, 206–216 (1985)], antagonists of CCK and gastrin are useful in treating these tumours [see, R. D. Beauchamp et al., *Ann. Surg.*, 202, 203 (1985)].

In the light of discussion in C. Xu et al., *Peptides*, 8, 1987, 769–772, CCK antagonists may also be effective in neuroprotection.

CCK receptor antagonists have been found to inhibit the contractile effects of CCK on iris sphincter and ciliary muscles of monkey and human eyes (Eur. J. Pharmacol., 211(2), 183–187; A. Bill et al., Acta Physiol. Scand., 138, 479–485 [1990]), thus having utility in inducing miosis for therapeutic purposes.

A class of benzodiazepine antagonist compounds has been reported which binds selectively to brain CCK (CCK-B and CCK-A) and gastrin receptors [see M. Bock et al., *J. Med Chem.*, 32, 13–16 (1989)].

European patent application no. 0 167 919 discloses benzodiazepine CCK and gastrin antagonists substituted in the 3-position by, inter alia, a phenyl urea and at the 5-position by an optionally substituted phenyl or $C_{1-4}$alkyl group. There is no suggestion of the phenyl urea substitution of the compounds of the present invention.

The present invention provides benzodiazepine compounds of formula (I)

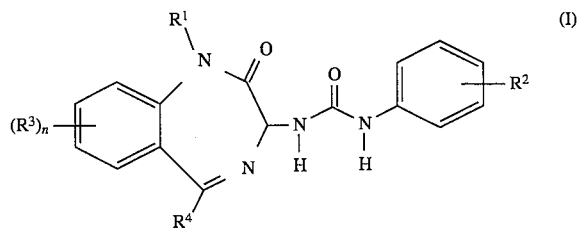

wherein:
$R^1$ represents H, $(CH_2)_q$imidazolyl, $(CH_2)_q$tetrazolyl, $(CH_2)_q$triazolyl, (where q is 1, 2 or 3); $C_{1-6}$alkyl optionally substituted by one or more groups selected from halo, hydroxy and $NR^6R^7$ (where $R^6$ and $R^7$ each independently represents H or $C_{1-4}$alkyl, or $R^6$ and $R^7$ together form a chain $(CH_2)_p$ where p is 4 or 5); $C_{3-7}$cycloalkyl; cyclopropylmethyl; $CH_2CO_2R^5$ (where $R^5$ is $C_{1-4}$alkyl), $CH_2CONR^6R^7$ or $CH_2CH(OH)$—W—$(CH_2)_2NR^6R^7$ where W is S or NH and $R^6$ and $R^7$ are as previously defined;

$R^2$ represents a group wherein:

X represents O, S or $NR^8$ where $R^8$ represents H or $C_{1-4}$alkyl;

one of Z and Y is C=O and the other is O, S or $NR^9$, where $R^9$ represents H or $C_{1-4}$alkyl;

$R^3$ represents $C_{1-6}$alkyl, $NR^6R^7$, where $R^6$ and $R^7$ are as previously defined, or halo;

$R^4$ represents $C_{3-10}$cycloalkyl;

n is 0, 1, 2 or 3;

and salts and prodrugs thereof.

As used herein, the definition of each expression, when it occurs more than once in any structure, is intended to be independent of its definition elsewhere in the same structure.

It will be appreciated that formula (I) is intended to embrace all possible isomers, including optical isomers, and mixtures thereof, including racemates.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bungaard, Elsevier, 1985.

As used herein, alkyl means linear or branched chain alkyl. Examples of suitable alkyl groups include methyl, ethyl, isopropyl and isobutyl groups.

When $R^1$ represents cycloalkyl, examples of suitable cycloalkyl groups include cyclopropyl, cyclopentyl and cyclohexyl groups, preferably cyclopropyl.

Halo includes fluoro, chloro, bromo and iodo. Preferably halo will be fluoro or chloro.

A subgroup of compounds of the present invention is represented by compounds of formula (I) wherein $R^3$ represents $C_{1-6}$alkyl or halo; $R^4$ represents $C_{3-7}$cycloalkyl; and n is 0, 1 or 2.

Preferably $R^1$ is $C_{1-6}$alkyl, more preferably $C_{1-4}$alkyl, such as methyl, n-propyl or isobutyl.

Suitable examples of the substituent $R^2$ include

Preferably $R^2$ represents oxadiazolinone.

Preferably $R^2$ is in the 3- or 4-position of the phenyl ring, more preferably the 3-position.

Suitable values for $R^3$ include methyl, dimethylamino, chloro and bromo.

Preferably n is 0 or 1, more preferably 0.

Suitable values for $R^4$ include cyclobutyl, cyclopentyl, cyclohexyl and cycloheptyl. Preferably $R^4$ represents cyclohexyl.

A preferred sub-group of compounds according to the invention is represented by compounds of formula (IA), and salts and prodrugs thereof:

wherein $R^4$ is as defined for formula (I) above and $R^{20}$ represents $C_{1-6}$alkyl, preferably $C_{1-4}$alkyl.

Preferably the salts of the compounds of formula (I) are pharmaceutically acceptable, but non-pharmaceutically acceptable salts may be used for the preparation of pharmaceutically acceptable salts. The pharmaceutically acceptable salts of the compounds of formula (I) include the conventional non-toxic salts or the quaternary ammonium salts of the compounds from formula (I) formed, e.g., from non-toxic inorganic or organic salts. For example, such conventional non-toxic salts include basic salts, e.g. sodium and potassium salts and those derived from inorganic acids such as hydrochloric, hydrobromic, sulphuric, sulphamic, phosphoric, nitric and the like; and the salts prepared from organic acids such as acetic, propionic, succinic, glycolic, steric, lactic, malic, tartaric, citric, ascorbic, palmoic, maleic, hydroxymaleic, phenylacetic, glutamic, benzoic, salicylic, sulphanilic, 2-acetoxy benzoic, fumaric, toluenesulphonic, methanesulphonic, ethane disulphonic, oxalic and isothionic.

The pharmaceutically acceptable salts of the present invention can be synthesized from the compound of formula (I) which contain a basic or acidic moiety by conventional chemical methods. Generally, the salts are prepared by reacting the free base or acid with stoichiometric amounts or with an excess of the desired salt-forming inorganic or organic acid or base in a suitable solvent or combination of solvents.

For example, an acid of formula (I) may be reacted with an appropriate amount of a base, such as an alkali or alkaline earth metal hydroxide e.g. sodium, potassium, lithium, calcium, or magnesium, or an organic base such as an amine, e.g. dibenzylethylenediamine, trimethylamine, piperidine, pyrrolidine, benzylamine, and the like, or a quaternary ammonium hydroxide such as tetramethylammonium hydroxide.

The compounds of formula (I) antagonise CCK and/or gastrin and are useful for the treatment and prevention of disorders including central nervous system disorders wherein CCK and/or gastrin may be involved. Examples of such disease states include gastrointestinal diseases, including gastrointestinal ulcers, such as peptic and duodenal ulcers, irritable bowel syndrome, gastroesophagenal reflux disease or excess pancreatic or gastrin secretion, acute pancreatitis, or motility disorders; central nervous system disorders, including central nervous system disorders caused by CCK interaction with dopamine, serotonin and other monoamine neurotransmitters, such as neuroleptic disorders, tardive dyskinesia, Parkinson's disease, psychosis or Gilles de la Tourette syndrome; depression; such as depression resulting from organic disease, secondary to stress associated with personal loss, or idiopathic depression; schizophrenia; disorders of appetite regulatory systems; Zollinger-Ellison syndrome, antral and cell hyperplasia, or pain.

The compounds of formula (I) are particularly useful in the treatment or prevention of neurological disorders involving anxiety disorders and panic disorders, wherein CCK and/or gastrin is involved. Examples of such disorders include panic disorders, anxiety disorders, panic syndrome, anticipatory anxiety, phobic anxiety, panic anxiety, chronic anxiety and endogenous anxiety.

The compounds of formula (I) are also useful for directly inducing analgesia, opiate or non-opiate mediated, as well as anesthesia or loss of the sensation of pain.

The compounds of formula (I) may further be useful for preventing or treating the withdrawal response produced by chronic treatment or abuse of drugs or alcohol. Such drugs include, but are not limited to benzodiazepines, cocaine, alcohol and nicotine.

The compounds of formula (I) may further be useful in the treatment of stress and its relationship with drug abuse.

The compounds of formula (I) may further be useful in the treatment of oncologic disorders wherein CCK may be involved. Examples of such oncologic disorders include small cell adenocarcinomas and primary tumours of the central nervous system glial and neuronal cells. Examples of such adenocarcinomas and tumours include, but are not limited to, tumours of the lower oesophagus, stomach, intestine, colon and lung, including small cell lung carcinoma.

The compounds of formula (I) may also be useful as neuroprotective agents, for example, in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by neurotoxins, including environmental neurotoxins.

The compounds of formula (I) may further be used to induce miosis for therapeutic purposes after certain types of examination and intraocular surgery. An example of intraocular surgery would include cateract surgery with implantation of an artificial lens. The CCK antagonist compounds of this invention can be used to prevent miosis occuring in association with iritis, ureitis and trauma.

The present invention therefore provides a compound of formula (I) or a salt or prodrug thereof for use in the preparation of a medicament.

The present invention also provides a compound of formula (I) or a salt or prodrug thereof for use in therapy.

In a further or alternative embodiment the present invention provides a method for the treatment or prevention of a physiological disorder involving CCK and/or gastrin which method comprises administration to a patient in need thereof of a CCK and/or gastrin antagonising amount of a compound of formula (I).

When a compound according to formula (I) is used as an antagonist of CCK or gastrin in a human subject, the daily dosage will normally be determined by the prescibing physician with the dosage generally varying according to the age, weight, and response of the individual patient, as well as the severity of the patient's symptoms. However, in most instances, an effective daily dosage wll be in the range from about 0.005 mg/kg to about 100 mg/kg of body weight, and preferably, of from 0.05 mg/kg to about 50 mg/kg, such as from about 0.5 mg/kg to about 20 mg/kg of body weight, administered in single or divided doses. In some cases, however, it may be necessary to use dosages outside these limits. For example, animal experiments have indicated that doses as low as 1 ng may be effective.

In effective treatment of panic syndrome, panic disorder, anxiety disorder and the like, preferably about 0.05 mg/kg to about 0.5 mg/kg of CCK antagonist may be administered orally (p.o.), administered in single or divided doses per day (b.i.d.). Other routes of administration are also suitable.

For directly inducing analgesia, anaesthesia or loss of pain sensation, the effective dosage preferably ranges from about 100 ng/kg to about 1 mg/kg by systemic administration. Oral administration is an alternative route, as well as others.

In the treatment or irritable bowel syndrome, preferably about 0.1 to 10 mg/kg of CCK antagonist is administered orally (p.o.), administered in single or divided doses per day (b.i.d.). Other routes of administration are also suitable.

The use of a gastrin antagonist as a tumour palliative for gastrointestinal neoplasma with gastrin receptors, as a modulator of central nervous activity, treatment of Zollinger-Ellison syndrome, or in the treatment of peptic ulcer disease, an effective dosage of preferably about 0.1 to about 10 mg/kg administered one-to-four times daily is indicated.

For use as neuroprotective agents the effective dosage preferably ranges from about 0.5 mg/kg to about 20 mg/kg.

Because these compounds antagonise the function of CCK in animals, they may also be used as feed additives to increase the food intake of animals in daily dosage of preferably about 0.05 mg/kg to about 50 mg/kg of body weight.

The compounds of formula (I) may be prepared by processes analogous to those described in European Patent Specification No. 0284256. For example, a compound of formula (I) may be prepared by reacting an intermediate of formula (II) with an intermediate of formula (III)

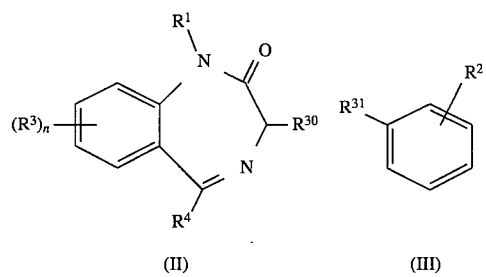

wherein $R^1$, $R^2$, $R^3$, $R^4$ and n are as defined for formula (I), and one of $R^{30}$ and $R^{31}$ represents $NH_2$ and the other of $R^{30}$ and $R^{31}$ represents —N=C=O.

The reaction is preferably conducted in a suitable organic solvent, such as an ether, for example, tetrahydrofuran, at room temperature.

Intermediates of formula (II) wherein $R^{30}$ represents $NH_2$ (IIA) may be prepared from compounds of formula (VI)

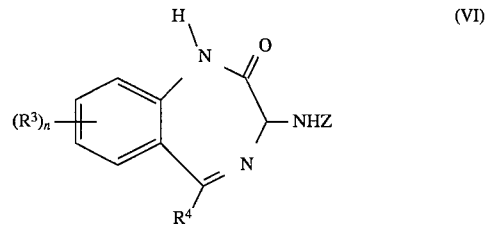

wherein $R^3$, $R^4$ and n are as defined for formula (I) and Z is a protecting group; by reaction with a reagent suitable to introduce the group $R^1$, for example a halide of formula $R^1$Hal where Hal represents halo such as bromo or iodo, in the presence of a base, such as an alkali metal hydride or an alkaline earth metal carbonate, for example sodium hydride or caesium carbonate; or a suitable dialkyl acetal of dimethyl formamide in a suitable organic solvent, e.g. toluene followed by deprotection.

Compounds of formula (VI) may be prepared from compounds of formula (VII)

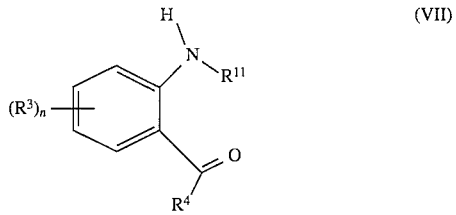

wherein $R^3$, $R^4$ and n are as defined for formula (I) and $R^{11}$ is H, by a reaction sequence comprising:

(i) reaction with a compound of formula (VIII)

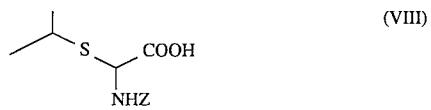

wherein Z is as defined above, in the presence of a base, such as a tertiary amine, for example triethylamine or N-methyl morpholine, and a coupling reagent. Any of the coupling reagents commonly used in peptide synthesis are suitable, for example, 1,3-dicyclohexylcarbodiimide (DCC), isobutyl chloroformate or, preferably, bis(2-oxo-3-oxazolidinyl)phosphinic chloride (BOP-Cl);

(ii) Treatment with gaseous ammonia, preferably in the presence of a mercury containing catalyst, such as mercury(II) chloride. The reaction is conveniently effected in a suitable organic solvent, such as an ether, for example, tetrahydrofuran;

(iii) Treatment with an organic acid, for example acetic or propionic acid, optionally in the presence of an ammonium salt, for example ammonium acetate.

Compounds of formula (VII) wherein $R^{11}$ is H may be prepared from corresponding compounds of formula (VII) wherein $R^{11}$ is $COCH_3$ by treatment with a mineral acid, for example hydrochloric acid, or base hydrolysis, for example, using aqueous sodium hydroxide. The reaction is conveniently affected in refluxing methanol.

Alternatively, compounds of formula (VII) wherein $R^{11}$ is H may be prepared by reaction of a compound of formula (IX)

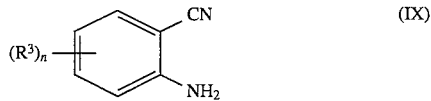

wherein $R^3$ and n are as previously defined, with a Grignard reagent of formula $R^4$MgHal wherein $R^4$ is as previously defined and Hal is halo such as chloro, bromo or iodo.

Compounds of formula (IX) are commercially available or may be prepared from commercially available compounds by conventional methods.

Compounds of formula (VII) wherein $R^{11}$ is $COCH_3$ may be prepared from compounds of formula (X)

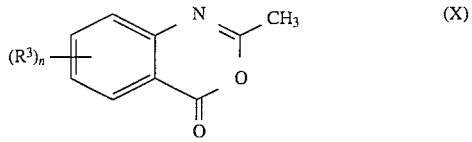

wherein $R^3$ and n are defined as for formula (I), by reaction with a Grignard reagent of formula $R^4$MgHal wherein Hal is halo such as chloro, bromo or iodo.

Compounds of formula (X) may be prepared by known methods, e.g. see D. A. Walsh, Synthesis, 677, (1980).

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-L-tartaric acid and/or (+)-di-p-toluoyl-D-tartaric acid followed by fractional crystallization and regeneration of the free base. The novel compounds may also be resolved by formation of diastereomeric esters or amides, followed by chromatographic separation and removal of the chiral auxiliary. Alternatively, enantiomers of the novel compounds may be separated by HPLC using a chiral column.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wutts, *Protective Groups in Organic Synthesis*, John Wiley & Sons, 1991. The protecting groups may be removed at a convenient subsequent stage using methods known from the art.

The following examples are provided to assist in a further understanding of the invention. Particular materials employed, species and conditions are intended to be further illustrative of the invention and not limitative of the scope thereof.

EXAMPLE 1

N-[3(R)-5-Cyclohexyl-2,3-dihydro-1-methyl-2-oxo-1H-1,4-benzodiazenin-3-yl] N'[3-(5-oxo-4H-1,2,4-oxadiazolin-3-l)phenyl] urea Intermediate 1

(+)-3(R)-Amino-5-cyclohexyl-1,3-dihydro-1-methyl-2H-1,4-benzodiazenin-2-one

Step 1: (2-Acetamidophenyl) cyclohexyl methanone

Cyclohexylmagnesium bromide (240 ml of a 2M solution in ether, 0.48 mol) in ether (200 ml) was added dropwise to a solution of 2-methyl-4H-3,1-benzoxazin-4-one (100 g, 0.62 mol) in ether (1100ml) at −10° C. over 2 h. The mixture was stirred at this temperature for 2 h, then at ambient temperature for 30 min. After cooling to −10° C. the suspension was treated with 2M HCl (600 ml), keeping the temperature below 0° C. After stirring for 15 min the layers were separated, and the ethereal layer washed sequentially with water (500 ml), 5% sodium hydroxide solution (2×500 ml) and finally water (2×500 ml). The organic layer was separated, dried (MgSO$_4$), evaporated in vacuo and chromatographed on silica using petrol:ethyl acetate (2:1). to give (2-acetamidophenyl) cyclohexyl methanone (28 g, 24%) as a pale yellow solid. mp 66° C. $^1$H NMR (CDCL$_3$, 360 MHz)_1.25–1.89 (10H, m), 2.23 (3H, s), 3.33 (1H, m), 7.13 (1H, dt, J=6 and 1 Hz), 7.53 (1H, dt, J=6 and 1 Hz), 7.92 (1H, d, J=6 Hz), 8.76 (1H, d, J=6 Hz), 11.73 (1H, brs).

Step 2: (2-Aminophenyl) cyclohexyl methanone

A solution of (2-acetamidophenyl) cyclohexyl methanone (0.53 g, 2.16 mmol) in methanol (5 ml) and concentrated hydrochloric add (15 ml) was heated at 80° C. for 1 h. After this time the solution was cooled to ambient temperature and the solvents removed in vacuo. The residue was dissolved in water (10 ml) and basified with 4N sodium hydroxide solution (20 ml). The mixture was then extracted into ethyl acetate (4×20 ml) and the organic layers combined and dried (MgSO$_4$). The solvent was evaporated and the residue chromatographed on silica gel, using petrol:ethyl acetate (2:1), to afford the amine (0.40 g, 91%) as a white solid. mp 73°–75° C. $^1$ H NMR (360 MHz, CDCL$_3$)_1.23–2.09 (10H, m), 3.27 (1H, m), 6.29 (2H, brs), 6.64 (2H, m), 7.25 (1H, dt, J=6 and 1 Hz), 7.76 (1H, dd, J -7 and 1 Hz).

An alternative procedure could be used for preparation of (2-aminophenyl)cyclohexyl methanone: To a cooled (0° C.) and stirred solution of 2-aminobenzonitrile (59.5 g, 0.5 mmol) in anhydrous diethyl ether (210 ml) was added dropwise cyclohexylmagnesium chloride (2M in diethyl ether, 700 ml) at such a rate as to maintain the temperature below 25° C. After a further 18 h stirring at room temperature, the mixture was cooled to −60° C. and treated dropwise (CAUTION! highly exothermic reaction) with 5N hydrochloric add (600 ml). The mixture was then allowed to warm to room temperature, diluted with additional 5N hydrochloric add (500 ml) and the ethereal layer was separated. The acidic aqueous solution was basified to pH 4–5 with solid potassium hydroxide and then extracted with ethyl acetate (3×700 ml). The ethereal and ethyl acetate solutions were combined, washed with brine (1000 ml), dried (MgSO$_4$) and concentrated under vacuum to give the title compound (97 g, 94%) as a pale yellow solid.

Step 3: 3(R,S)-[(Benzyloxycarbonyl)amino]-5-cyclohexyl-1,3-dihydro-2H-1,4-benzodiazepin-2-one α-(Isopropylthio)-N-(benzyloxycarbonyl)glycine (30 g, 0.11 mol) was dissolved in dichloromethane (1000 ml) and cooled to 0° C. The stirred solution was then treated with N-methyl morpholine (11.5 ml, 0.11 mol) followed by isobutyl chloroformate (13.7 ml, 0.11 mol). The resulting reaction mixture was stirred for a further 15 min at 0° C., then heated to reflux. The refluxing reaction mixture was treated dropwise, over 20 min, with a solution of (2-aminophenyl) cyclohexyl methanone (20.5 g, 0.1 mmol) in dichloromethane (140 ml). After addition was complete the reaction was heated at reflux for a further 4 h. The mixture was then washed in succession with 10% citric acid solution (2×500 ml), saturated sodium bicarbonate solution (2×500 ml) and brine (500 ml). The dried (MgSO$_4$) organic phase was evaporated to afford the crude product as a pale orange solid, which was used without further purification.

The crude (isopropylthio)glycinamide was dissolved in anhydrous tetrahydrofuran (800 ml) and cooled to 0° C. Ammonia gas was bubbled through the stirred solution for 30 min before adding mercuric chloride (33 g, 0.12 mol) in one portion. Ammonia was continually bubbled through the solution for a further 5 hours, then the suspended solids were filtered off. The solvent was evaporated in vacuo to leave an oil, which was used without further purification.

The crude α-aminoglycinamide was dissolved in glacial acetic acid (500 ml) and treated with ammonium acetate (36.2 g, 0.47 mol). The resulting reaction mixture was stirred at room temperature overnight, before removing the solvent in vacuo. The residue was partitioned between ethyl acetate (300 ml) and 1N sodium hydroxide solution (300 ml). The organic phase was separated, dried (MgSO$_4$) and evaporated. The residue was chromatographed on silica, using 2:1 petrol:ethyl acetate as the eluant, to afford 3(R,S)-[(benzyloxycarbonyl)amino]-5-cyclohexyl-1,3-dihydro-2H-1,4-benzodiazepin-2-one (25 g, 64%) as a white solid. mp 164–166° C. $^1$H NMR (360 MHz, CDCL$_3$) δ1.07–2.04 (10H, m), 2.77 (1H, m), 5.12 (3H, m), 6.44 (1H, d, J=8 Hz), 7.08 (1H, d, J=8 Hz), 7.23–7.36 (6H, m), 7.46 (1H, t, J=7 Hz), 7.59 (1H, d, J=8 Hz), 8.60 (1H, brs).

Step 4: 3(R,S)-[(Benzyloxycarbonyl)amino]-5-cydohexyl-1,3-dihydro-1-methyl-2H-1,4-benzodiazepin-2-one A solution of 3(R,S)-[(benzyloxycarbonyl)amino]-5-cyclohexyl-1,3-dihydro-2H-1,4-benzodiazepin-2-one (1.1 g, 2.8 mmol) in dimethylformamide (13 ml), under an atmosphere of nitrogen, was treated with sodium hydride (117 mg of a 55–60% dispersion in mineral oil, 2.8 mmol) in one portion, at −10° C. After 30 min at −10° C., iodomethane (174 μl, 2.8 mmol) was added in one portion and the solution allowed to reach 0° C. over 1 h. The solvent was then removed in vacuo and the crude residue partitioned between water (100 ml) and dichloromethane (100 ml). The organic phase was separated and the aqueous phase extracted with dichloromethane (2×100 ml). The combined organic layers were washed with brine, dried (MgSO$_4$) and evaporated. The residue was chromatographed on silica, using 1:1 petrol:ethyl acetate as the eluant, to afford the title compound (0.75 g, 66%) as a white solid. mp 205–207° C. $^1$H NMR (360 MHz, CDCl$_3$) δ1.03–2.04 (10H, m), 2.76 (1H, m), 3.36 (3H, s), 5.10 (3H, m), 6.52 (1H, d, J=8 Hz), 7.25–7.55 (9H, m).

Step 5: 3(R,S)-Amino-5-cyclohexyl-1,3-dihydro-1-methyl-2H-1,4-benzodiazepin-2-one A mixture of 3(R,S)-[(benzyloxycarbonyl)amino]-5-cyclohexyl-1,3-dihydro-1-methyl-2H-1,4-benzodiazepin-2-one (3.0 g, 7.4 mmol) and hydrobromic acid (45% in acetic acid, 6.2 ml) was stirred for 1 h at room temperature under an atmosphere of nitrogen. The mixture was then diluted with cold anhydrous diethyl ether (40 ml) and it was stirred at 0° C. for 45 min. The white precipitate was collected by filtration, washed with cold diethyl ether (4×30 ml) and then dissolved in a mixture of water (30 ml) and aqueous sodium hydroxide (2M, 15 ml). The basic aqueous phase was extracted with ethyl acetate (3×70 ml) and the combined organic layers were washed with brine (30 ml), dried (Na$_2$SO$_4$) and concentrated. The residue was chromatographed on silica gel using 94:6, dichloromethane: methanol as the eluant, to afford the title compound (1.6 g, 80%) as pale pink solid. mp 133–136° C. $^1$H NMR (360 MHz, CDCl$_3$)δ1.02–1.40 (4H, m), 1.47–1.56 (1H, m), 1.61–1.74 (3H, m), 1.84–1.91 (1H, m), 1.96–2.06 (1H, m), 2.17 (2H, br s), 2.70–2.80 (1H, m), 3.39 (3H, s), 4.29 (1H, s), 7.20–7.27 (2H, m), 7.44–7.54 (2H, m).

Step 6: 3(R,S)-[2(R)-(tert-Butyloxycarbonyl)amino-3-phenylpropionylamino]-5-cyclohexyl-1,3-dihydro-1-methyl-2H-1,4-benzodiazenin-2-one To a solution of 3(R,S)-amino-5-cyclohexyl-1,3-dihydro-1-methyl-2H-1,4-benzodiazepin-2-one (4 g, 14.8 mmol) in anhydrous dimethylformamide (35 ml), under an atmosphere of nitrogen, was added in succession Boc-D-phenylalanine (4.11 g, 15.4 mmol), 1-hydroxybenzotriazole trihydrate (2.09 g, 15.4 mmol) and 1-ethyl-3-[3-(dimethylamino)propyl]carbodiimide hydrochloride (2.97 g, 15.4 mmol). Triethylamine (2.16 ml, 15.4 mmol) was then added and the resulting suspension was stirred at ambient temperature for 20 min. The solvent was removed under reduced pressure and the residue was partitioned between ethyl acetate (50 ml) and 10% citric acid solution (50 ml). The organic phase was separated and the aqueous phase extracted with ethyl acetate (3×50 ml). The combined organic phases were washed with 10% sodium hydroxide solution (50 ml), water (50 ml) and brine (50 ml), dried (MgSO$_4$) and evaporated in vacuo. The residue was chromatographed on silica, using 1:1 petrol:ethyl acetate as the eluant, to afford the product (7.26, 95%) as a pale yellow solid. mp 95–98° C. $^1$H NMR (360 MHz, CDCl$_3$) δ0.99–1.11 (1H, m), 1.16–1.72 (7H, m), 1,40 (9H, s), 1.83–1.92 (1H, m), 1.98–2.06 (1H, m), 2.73–2.83 (1H, m), 3.10–3.24 (2H, m), 3.38 (3H, s), 4.53 (1H, brs), 4.98 (1H, brs), 5.28–5.34 (2H, m), 7.19–7.32 (7H, m), 7.49–7.58 (2H, m).

Step 7: (+)-3(R)-(2(R)-Amino-3-phenylpropionylamino)-5-cyclohexyl-1,3-dihydro-1-methyl-2H-1,4-benzodiazepin-2-one 3(R,S)-[2(R)-(tert-Butyloxycarbonyl)amino-3-phenylpropio nylamino]-5-cyclohexyl-1,3-dihydro-1-methyl-2H-1,4-benzodiaze pin-2-one (4.7 g, 9.1 mmol) was dissolved in ethyl acetate (20 ml) and cooled to 0° C. This solution was then saturated with hydrogen chloride gas. After 1 h 30 min, the resulting precipitate (which was shown to be the undesired diastereoisomer, R$_f$=0.04 ethyl acetate), was removed by filtration and the filtrate evaporated. The solid residue was partitioned between ethyl acetate (25ml) and 10% sodium carbonate solution (20 ml). The 25 organic phase was separated and the aqueous extracted with ethyl acetate (2×25 ml). The combined organic phases were dried (Na$_2$SO$_4$) and evaporated in vacuo. The residue was chromatographed on silica using a gradient elution of 0–20% methanol in ethyl acetate to afford the title compound (1.66 g, 44%, R$_f$=0.13 ethyl acetate) as a pale yellow solid. mp 100–103° C. $^1$H NMR (360 MHz, CDCl$_3$) δ1.00–1,39 (4H, m), 1.50–1.72 (4H, m), 1.84–1.92 (1H, m), 2.00–2.07 (1H, m), 2.72–2.84 (1H, m), 2.79 (1H, dd, J=13.8 and 9.8 Hz), 3.28 (1H, dd, J=13.8 and 4.0 Hz), 3.40 (3H, s), 3.69 (1H, dd, J=9.8 and 4.1 Hz), 5.36 (1H, d, J=8.3 Hz), 7.21–7.36 (7H, m), 7.47–7.58 (2H, m), 8.66 (1H, d, J=8.3 Hz). [α]$^{23}$$_D$ +32.7°(c=0.58,CH$_3$OH).

The undesired diastereoisomer (Rf 0.04, ethyl acetate) could be epimerised to 3(R,S)-(2(R)-amino-3-phenylpropionylamino)-5-cyclohexyl-1,3-dihydro-1-methyl-2H-1,4-benzodiazepin-2-one using the following procedure:

The undesired diastereoisomer (Rf 0.04, ethyl acetate) (16.8 g, 0.044 mol) was dissolved in anhydrous ether (200 ml), and potassiuxn-tert-butoxide (0.68 g, 6.1 mmol) was added. The mixture was stirred at room temperature for 1 h, then more potassium-tert-butoxide (0.68 g, 6.1 mmol) was added and the mixture heated at reflux for 5 h. The mixture was then cooled to ambient temperature, the solvent removed under vacuum, and the residue partitioned between ethyl acetate (200ml) and water (200 ml). The organic layer was separated, dried (MgSO$_4$), filtered and evaporated in vacuo to afford the epimerised material.

Step 8: (+)-N-[1(R)-2-[(3(R)-5-Cyclohexyl-2,3-dihydro-1-methyl-2-oxo-1H-1,4-benzodiazepin-3-yl)amino]-2-oxo-1-(phenyl methyl)ethyl]N'-phenyl thiourea A solution of (+)-3(R )-(2(R)-amino-3-phenylpropionylamino)-5-cyclohexyl-1,3-dihydro-1-methyl-2H -1,4-benzodiazepin-2-one (1.6 g, 3.83 mmol) in anhydrous dichloromethane (10 ml) was treated with phenyl isothiocyanate (0.5 ml, 4.21 mmol), and then heated on the steam bath for 30 min. The solvent was evaporated in vacuo and the residue was chromatographed on silica with 1:1, ethyl acetate:petrol to afford the product (2.1 g, 100%) as a pale yellow solid. mp 129–132° C. $^1$H NMR (360 MHz, CDCl$_3$) δ0.95–1.07 (1H, m), 1.15–1.37 (3H, m), 1.45–1.69 (4H, m), 1.81–1.88 (1H, m), 1.93–2.00 (1H, m), 2.70–2.80 (1H, m), 3.24–3.41 (2H, m), 3.38 (3H, s), 5.23 (1H, d, J=7.3 Hz), 5.31–5.40 (1H, m), 6.67 (1H, 7.0 Hz), 6.87–7.02 (2H, m), 7.20–7.35 (9H, m), 7.46–7.52 (2H, m), 7.65 (1H, s). [α]$^{25}$$_D$+27.3°(c=0.31, CH$_2$Cl$_2$).

Step 9: (+)-3(R)-Amino-5-cyclohexyl-1,3-dihydro-1-methyl-2H-1,4-benzodiazepin-2-one N-[1(R)-2-[(3(R)-5-Cyclohexyl-2,3-dihydro-1-methyl-2-oxo-1H-1,4-benzodiazepin-3-yl)amino]-2-oxo-1-(phenylmethyl)ethyl]N'-phenyl thiourea (4.5 g, 8.1 mmol ) was dissolved in trifiuoroacetic acid (25 ml) and stirred at ambient temperature for 30 min. The trifluoroacetic acid was removed under reduced pressure and the residue azeotroped with dichloromethane (2×20 ml) and toluene (2×20 ml). The residue was chromatographed on silica gel using 90:10:0.1:0.1, dichloromethane: methanol:acetic add:water as the eluant to afford an orange gum. This was dissolved in ethyl acetate (150 ml), cooled to 0° C., and treated with 10% sodium carbonate solution (15 ml). After diluting with water (25 ml) and stirring for 1 min, the organic layer was separated and the aqueous re-extracted with ethyl acetate (2×50 ml). The combined organics were dried (Na$_2$SO$_4$) and evaporated in vacuo to afford the title compound (1.56 g, 71%) as a solid with 99% e.e. mp 133–136° C. $^1$H NMR (360 MHz, CDCl$_3$) δ1.01–1.39 (4H, m), 1.50–1.54 (1H, m), 1.60–1.70 (3H, m), 1.84–1.92 (1H, m), 1.96–2.04 (1H, m), 2.36 (2H, brs), 2.70–2.80 (1H, m), 3.41 (3H, s), 4.32 (1H, s), 7.22–7.28 (2H, m), 7.46–7.58 (2H, m). [α]$^{23}$$_D$+33.2°(c= 0.66,CH$_3$OH).

Intermediate 2

1-(5-Oxo-4H -1,2,4-oxadiazolin-3-yl)-3-aminobenzene hydrochloride salt

Step 1: 1-Cyano-3-tert-butyloxycarbonylaminobenzene

To a solution of 3-minobenzonitrile (47 g, 0.40 mol) in dichloromethane (210 ml) was added a solution of di-tert-butyldicarbonate (132 g, 0.60 mmol) in dichloromethane (150 ml). The mixture was heated at reflux for 4 days then the mixture cooled to room temperature, and stirred with 10% citric acid solution (200 ml). The organic layer was separated and the aqueous phase extracted with dichloromethane (3×100 ml). The organic layers were combined, washed with brine (100 ml) then separated. After drying (Na$_2$SO$_4$) the solvent was evaporated to afford a beige solid. This was triturated in petroleum ether (60/80) and the desired product collected as a white solid (65.9 g, 7.5%). mp 123–126° C. $^1$H NMR (360 MHz, CDCl$_3$)δ1.52 (9H, s), 6.50 (1H, brs), 7.29 (1H, d, J=8 Hz), 7.36 (1H, dd, J=8 and 8 Hz), 7.51 (1H, d, J=8 Hz), 7.76 (1H, s).

Step 2: 3-tert-Butyloxycarbonylaminobenzamide oxime

Hydroxylamine hydrochloride (3.16 g, 0.045 mol) was added to a stirred solution of sodium ethoxide in ethanol [prepared by dissolving 1.17 g of sodium in 70 ml of ethanol]. The mixture was stirred at room temperature for 15 min then 1-cyano-3-tert-butyloxycarbonylaminobenzene (3.00 g, 0.014 mol) was added. The mixture was heated at 50° C. overnight then cooled to ambient temperature. The mixture was then filtered and the filtrate evaporated in vacuo. The residue was partitioned between ethyl acetate (50 ml) and water (50 ml). The organic phase was separated and the aqueous phase extracted with ethyl acetate (3×20 ml). The organic layers were combined, washed with brine (50 ml) then dried ($Na_2SO_4$). The solvent was evaporated to leave a pink fo.m. The foam was left at 0° C. overnight, then triturated with 1:1 petrol:ethyl acetate. The title compound was collected as a white solid (2.52 g, 73%). $^1$H NMR (360 MHz, $D_6$-DMSO)δ1.47 (9H, s), 5.69 (2H, brs), 7.24 (2H, m), 7.41 (1H, brd, J=6.5 Hz), 7.82 (1H, s), 9.35 (1H, s), 9.58 (1H, s). MS (CI, $NH_3$) 252 (M+1).

Step 3: 1-(5-Oxo-4H-1,2,4-oxadiazolin-3-yl)-3-tert-butyloxycarbonlylaminobenzene To a stirred solution of the amide oxime (0.68 g, 2.7 mmol) in tetrahydrofuran (10 ml) was added 1,1-carbonyldiimidazole (0.53 g, 3.3 mmol). The solution was stirred at room temperature overnight, after which time a white solid had precipitated from solution. The mixture was then heated at reflux for 5 h then allowed to cool to ambient temperature. The solvent was removed in vacuo and the residue partitioned between dichloromethane (50 ml) and 10% citric add solution (50 ml). The organic layer precipitated a white solid which was collected by filtration. The solid was identified as the desired oxadiazolinone (0.53 g, 71%). mp 186–189° C. $^1$H NMR (360 MHz, $D_6$-DMSO)δ1.49 (9H, s), 7.36 (1H, d, J=9 Hz), 7.44 (1H, dd, J=8 and 8 Hz), 7.58 (1H, d, J=9 Hz), 8.07 (1H, s), 9.64 (1H, s), 13.00 (1H, brs).

Step 4: 1-(5-Oxo-4H-1,2,4-oxadiazolin-3-yl)-3-aminobenzene hydrochloride salt 1-(5-Oxo-4H-1,2,4-oxadiazolin-3-yl)-3-tert-butyloxycarbony laminobenzene (0.8 g, 2.9 mmol) was dissolved in ethyl acetate (40 ml) and cooled to 0° C. Hydrogen chloride gas was then bubbled through the stirred solution for 10 min. Nitrogen was bubbled through the mixture for 10 min then the solvent evaporated in vacuo. The residue was azeotroped with toluene (2×20 ml) then triturated with ether. The title compound (0.59 g, 95%) was isolated as a white solid. mp 238–242° C. (dec.). 1H NMR (360 MHz, $D_6$-DMSO) δ7.33 (1H, m), 7.51–7.54 (3H, m).

N-[3(R)-5-Cyclohexyl-2,3-dihydro-1-methyl-
2-oxo-1H-1,4-benzodiazepin-3-yl
]N'-[3-(5-oxo-4H-1,2,4-oxadiazolin,3-yl)
phenyl]urea A suspension of 1-(5-oxo-4H-1,2,4-oxadiazolin-3-yl)-3-aminobenzene hydrochloride salt [Intermediate 2] (281 mg, 1.3 mmol) in anhydrous tetrahydrofuran (25 ml), under nitrogen, was treated with triethylamine (0.36 ml, 2.6mmol) dropwise. The mixture was then cooled to 0° C. and triphosgene (127 mg, 0.43 mmol) added, followed by triethylamine (0.36 ml, 2.6 mmol) dropwise. The mixture was stirred at 0° C. for 5 min then the cooling bath removed and stirred at ambient temperature for 10 min. The mixture was then cooled to 0° C. and a solution of (+)-3R)-amino-5-cyclohexyl-1,3-dihydro-1-methyl-2H-1,4-benzodiazepin-2-one [Intermediate 1 ] (245 mg, 0.9 mmol) in anhydrous tetrahydrofuran (4 ml) added dropwise. After addition the suspension was stirred at 0° C. for 5 min, then the cooling bath was removed and the mixture stirred at room temperature for 30 min. The mixture was then filtered and the filtrate evaporated in vacuo. The residue was partitioned between ethyl acetate (20 ml) and 20% aqueous acetic acid (20 ml). The organic layer was separated and washed once more with 20% aqueous acetic acid (20 ml) followed by brine (20ml). The organic phase was separated, dried ($Na_2SO_4$) and evaporated. The residue was chromatographed on silica gel, eluting with dichloromethane:methanol (97:3), to afford the desired product as a viscous oil. This was azeotroped with dichloromethane (2×20 ml) followed by toluene (2×20 ml). The resultant white solid was then triturated with anhydrous ether to afford the desired urea (310 mg, 73%) as a white solid. mp 216–218° C. (petrol (60/80)/EtOAc). $^1$H NMR (360 MHz, $D_6$-DMSO) δ0.91 (1H, m), 1.09t1.91 (9H, m), 2.93 (1H, m), 3.32 (3H, s), 5.07 (1H, d, J=8 Hz), 7.32–7.44 (4H, m), 7.55 (2H, m), 7.64 (1H, dd, J=8 and 8 Hz), 7.75 (1H, d, J=8 Hz), 7.91 (1H, s), 9.25 (1H, s).

EXAMPLE 2

N-[3(R,S)-5-Cyclobutyl-2,3-dihydro-1-methyl-
2-oxo-1H-1,4-benzodiazepin-3-yl]N'-
[3-(5-oxo-4H-1,2,4-oxadiazolin-3-yl) phenyl]urea Step 1: 2-Aminophenyl cyclobutyl methanone Over a period of 1 h a solution of cyclobutylbromide (13 g, 0.1 mmol) in diethyl ether (150 ml) was added dropwise to a slurry of magnesium turnings (2.5 g, 0.11 mol) and a crystal of iodine in diethyl ether (20 ml) at reflux. The mixture was stirred for a further hour whereupon the Grignard solution was cannulated into a pressure equalising dropping funnel, attached to a three-necked round-bottomed flask, which was under an atmosphere of nitrogen.

A solution of aminobenzonitrile (3.78 g, 32 mmol) at 0° C. in diethyl ether (50 ml) was treated dropwise with the Grignard reagent prepared above, over a period of 15 min.

Once the addition was complete, the mixture was warmed to room temperature and stirred for 16 h under nitrogen. The solution was cooled to 0° C., quenched with 5N hydrochloric acid (20 ml), and basified using solid sodium hydroxide (4 g). The aqueous solution was extracted with ethyl acetate (2×100 ml) and the combined organic layers were dried ($Na_2SO_4$) and evaporated. The residue was chromtographed on silica gel using 2:1 petrol: ethyl acetate as the eluant. This gave a yellow oil which was then azeotroped with toluene (2×80 ml) to give the title compound (4 g, 71%) as a pale yellow solid. mp 55° C. $^1$H NMR (250 MHz, $CDCl_3$)δ1.72–2.48 (6H, m), 3.80–4.00 (1H, m), 6.23 (2H, brs), 6.50–6.61 (2H, m), 7.11–7.22 (1H, m), 7.45–7.54 (1H m).

Step 2: 3(R,S)-[(Benzyloxycarbonyl)amino]-5-cyclobutyl-1,3-dihydro-2H-1,4-benzodiazepin-2-one A solution of α-isopropylthio-N-benzyloxycarbonyl glycine (8.4 g, 29.7 mmol) in anhydrous dichloromethane (200 ml) was cooled to 0° C. N-Methylmorpholine (3.3 ml, 29.7 mmol) was added over 2 min followed by isobutyl chloroformate (3.9 ml, 29.7 mmol). This mixture was stirred for 15 min at 0° C. whereupon the mixture was heated to reflux. 2-Aminophenyl cyclobutyl methanone (4 g, 22.9 mmol ) in anhydrous dichloromethane (20 ml) was added dropwise at reflux to the reaction mixture over 10 min and the mixture stirred at reflux for a further 1.5 h. The reaction mixture was washed with 1N citric add (100 ml), water (100 ml), saturated sodium bicarbonate solution (100 ml) and brine (100 ml). The organic phase was dried ($Na_2SO_4$), evaporated and azeotroped with toluene (2×100 ml) to give a yellow oil. Trituration with 7:1 petrol:ethyl acetate afforded the product (8 g, 80%) as a colourless solid. This material was used without further purification.

A solution of anhydrous tetrahydrofuran (300 ml) was cooled to 0° C. and saturated with ammonia gas. To this solution was added the glycinamide (8 g, 18 mmol) prepared above, followed by mercuric chloride (7.4 g, 27 mmol). The mixture was stirred at 0° C. for 1.5 h with continuous bubbling of ammonia gas. The mixture was filtered through "hyflo" and the filtrate evaporated to afford the desired amine as a colourless waxy solid. The material was used without further purification.

The amine (6.9 g, 18 mmol) prepared above was dissolved in acetic add (250 ml) and treated with ammonium acetate (6.5 g, 84.6 mmol). This mixture was stirred at room temperature for 16 h under nitrogen. The solvent was evaporated and the residue partitioned between ethyl acetate (250 ml) and 10% sodium hydroxide solution (100 ml). The organic was separated, dried ($Na_2SO_4$) and evaporated to give a yellow solid. Trituration with diethyl ether afforded the title compound (3.8 g, 50%) as a colourless solid. mp 200–202° C. TLC (silica, petrol:ethyl acetate 2:1). Rf=0.3. $^1$H NMR (250 MHz, $CDCl_3$)δ1.60–2.80 (6H, m), 3.70 (1H, m), 5.12 (2H, m), 5.22 (1H, d, J: 8 Hz), 6.50 (1H, d, J=8 Hz), 7.02–7.53 (9H, m), 9.44 (1H, s).

Step 3: 3(R,S)-[(BenzyloxVcarbonyl)amino]-5-cyclobutyl-1,3- dihydro-1-methyl-2H-1,4-benzodiazepin-3-one 3(R,S)-[(Benzyloxycarbonyl)amino]-5-cyclobutyl-1,3-dihydro-2H-1,4-benzodiazepin-2-one (1 g, 2.75 mmol) in anhydrous toluene (70 ml) was heated to reflux. A solution of dimethylformamide dim ethyl acetal (1.75 ml, 13.7 mmol) in anhydrous toluene (10 ml) was added dropwise and the mixture was heated at reflux for a further 3 h. The solvent was evaporated and the residue triturated with diethyl ether to afford the tifie compound (0.75 g, 72%) as a colourless solid. mp 210–211° C. $^1$H NMR (250 MHz, $CDCl_3$)δ1.68–2.06 (4H, m), 2.20–2.60 (2H, m), 3.41 (3H, s), 3.60–3.80 (1H, m), 5.00–5.30 (3H, m), 6.51 (1H, d, J: 14 Hz), 7.14–7.54 (9H, m).

Step 4: 3(R,S)-Amino-5-cyclobutyl-1,3-dihydro-1-methyl-2H-1,4-benzodiazenin-2-one 3(R,S)-[(Benzloxycarbonyl)amino]-5-cyclobutyl-1,3-dihydro-1-methyl-2H-1,4-benzodiazepin-2-one (400 mg, 1.06 mmol) was treated with a solution of 45% hydrogen bromide in acetic add (10 ml), and stirred for 20 min at room temperature. The mixture was then added dropwise onto cold (0° C.) diethyl ether (50 ml). A white solid was precipitated and filtered off. The solid was treated with 10% sodium hydroxide solution (50 ml), then extracted with ethyl acetate (80 ml). The organic layer was separated, dried ($Na_2SO_4$) and evaporated to give a yellow foam. This material was then used without further purification.

Step 5: N-[3(R,S)-5-Cyclobutyl-2,3-dihydro-1-methyl-2-oxo-1H-1,4-benzodiazepin-3-yl]N'[3-(5-oxo-4H-1,2,4-oxadiazolin-3-yl)phenyl]urea A suspension of 1-(5-oxo-4H-1,2,4-oxadiazolin-3-yl)-3-aminobenzene hydrochloride (330 mg, 1.54 mmol) in anhydrous tetrahydrofuran (25 ml) was treated with triethylamine (428 μl, 3.08 mmol) and stirred at room temperature for 5 min. The mixture was cooled to 0° C. whereupon triphosgene (151 mg, 0.51 mmol) was added. The mixture was stirred at 0° C. for 2 min, then triethylamine (428 μl, 3.08 mmol) was added dropwise to adjust the solution to pH 9. The mixture was then stirred for a further 5 min, allowed to warm to 15° C., and then re-cooled to 0° C. Then a solution of 3(R,S)-amino-5-cyclobutyl-1,3-dihydro-1-methyl-2H-1,4-benzodiazepin-2-one (251 mg, 1.06 mmol) in anhydrous tetrahydrofuran (4 ml) was added dropwise over 5 min. The mixture was stirred at 0° C. for 5 min, allowed to warm to room temperature and then stirred for a further 40 min. The undissolved material was removed by filtration. The solvent was evaporated in vacuo and the residue partitioned between ethyl acetate (20 ml) and 20% aqueous acetic add (10 ml). The organic phase was separated, dried ($Na_2SO_4$) and evaporated. The residue was chromatographed on silica gel with a 0.5% gradient elution of MeOH in dichloromethane. Trituration with diethyl ether afforded the product (130 mg, 25%) as a colourless solid. mp 225° C. (dec.). $^1$H NMR (360 MHz, $D_6$-DMSO)δ1.72–1.87 (1H, m), 1.92–2.12 (3H, m), 2.27–2.42 (1H, m), 2.46–2.59 (1H, m), 3.43 (3H, s), 3.72–3.84 (1H, m), 5.38 (1H, d, J=6 Hz), 7.22–7.66 (8H, m), 7.70 (1H, d, J=8 Hz), 7.81 (1H, s), 9.03 (1H, s).

EXAMPLE 3

N-[3(R,S)-5-Cyclohexyl-2,3-dihydro-1-methyl-2-oxo-1H-1,4-benzodiazepin-3-yl]N'-[3-(5-oxo-4H-1,2,4-oxadiazolin-3-yl) phenyl]urea A suspension of 1-(5-oxo-4H-1,2,4-oxadiazolin-3-yl)-3-aminobenzene hydrochloride salt [Intermediate 2] (57 mg, 0.27 mmol) in anhydrous tetrahydrofuran (5 ml), under nitrogen, was treated with triethylamine (75 μl, 0.55 mmol) dropwise. The mixture was then cooled to 0° C. and triphosgene (26 mg, 0.09 mmol) added, followed by triethylamine (75 μl, 0.55 mmol) dropwise. The mixture was then stirred at 0° C. for 5 min then the cooling bath removed and stirred at ambient temperature for 10 min. The mixture was then cooled to 0° C. and a solution of 3(R,S)-amino-5-cyclohexyl-1,3-dihydro-1-methyl-2H-1,4-benzodiazepin-3-one [Intermediate 1, Step 5] in anhydrous tetrahydrofuran (3 ml) added dropwise. After addition the suspension was stirred at 0° C. for 5 min, then the cooling bath was removed and the mixture stirred at room temperature for 30 min. The mixture was then filtered and the filtrate evaporated in vacuo. The residue was partitioned between ethyl acetate (20 ml) and 20% aqueous acetic acid (20 ml). The organic layer was separated and washed once more with 20% aqueous acetic acid (20 ml) followed by brine (20 ml). The organic phase was separated, dried ($Na_2SO_4$) and evaporated. The residue was treated with dichloromethane:methanol (97:3) and the undissolved solid filtered off. The white solid (35 mg, 41%) was identified as the desired urea. The filtrate was chromatographed on silica gel, eluting with dichloromethane:methanol (97:3), to afford the title compound (9 mg, 10%) as a white solid. mp 197–199° C. $^1$H NMR data was as described for Example 1.

EXAMPLE 4A

Tablets containing 1–25 mg of compound

|  | Amount mg | | |
|---|---|---|---|
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 4B

Tablets containing 26–100 mg of compound

|  | Amount mg | | |
| --- | --- | --- | --- |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 5

Parenteral injection

|  | Amount mg |
| --- | --- |
| Compound of formula (I) | 1 to 100 |
| Citric Acid Monohydrate | 0.75 |
| Sodium Phosphate | 4.5 |
| Sodium Chloride | 9 |
| Water for Injections | to 1 ml |

The sodium phosphate, citric acid monohydrate and sodium chloride are dissolved in a portion of the water. The compound of formula (I) is dissolved or suspended in the solution and made up to volume.

EXAMPLE 6

Topical formulation

|  | Amount mg |
| --- | --- |
| Compound of formula (I) | 1–10 |
| Emulsifying Wax | 30 |
| Liquid paraffin | 20 |
| White Soft Paraffin | to 100 |

The white soft paraffin is heated until molten. The liquid paraffin and emulsifying wax are incorporated and stirred until dissolved. The compound of formula (I) is added and stirring continued until dispersed. The mixture is then cooled until solid.

BIOLOGICAL ACTIVITY

1. CCK Receptor Binding (Pancreas)

CCK-8 sulphated was radiolabelled with $^{125}$I-Bolton Hunter reagent (2000 Ci/mmole). Receptor binding was performed according to Chang and Lotti (Proc. Natl. Acad. Sci. 83, 4923–4926, 1986) with minor modifications.

Male Sprague-Dawley rats (150–200 g) were sacrificed by decapitation. The whole pancreas was dissected free of fat tissue and was homogenized in 25 volumes of ice-cold 10 mM N-2-hydroxyethyl-piperazine-N'-2-ethane sulphonic acid (HEPES) buffer with 0.1% soya bean trypsin inhibitor (pH 7.4 at 25° C.) with a Kinematica Polytron. The homogenates were centrifuged at 47,800 g for 10 min. Pellets were resuspended in 10 volumes of binding assay buffer (20mM (HEPES)), 1 mM ethylene glycol-bis-(β-aminoethylether-N,N'-tetraacetic acid) (EGTA), 5 mM MgCl$_2$, 150 mM NaCl, bacitracin 0.25 mg/ml, soya bean trypsin inhibitor 0.1 mg/ml, and bovine serum albumin 2 mg/ml pH 6.5 at 25° C.) using a Teflon (trademark) homogenizer, 15 strokes at 500 rpm. The homogenate was further diluted in binding assay buffer to give a final concentration of 0.5 mg original wet weight/1 ml buffer. For the binding assay, 50 μl of buffer (for total binding) or unlabelled CCK-8 sulphated to give a final concentration of 1 μM (for nonspecific binding) or the compounds of Formula I (for determination of inhibition of $^{125}$I-CCK-8 binding) and 50 μl of 500 pM $^{125}$I-CCK-8 (i.e. 50 pM final concentration) were added to 400 μl of the membrane suspensions in microfuge tubes. All assays were run in duplicate. The reaction mixtures were incubated at 25° C. for 2 hours and the reaction terminated by rapid filtration (Brandell 24 well cell harvester) over Whatman GF/C filters, washing 3×4 mls with ice-cold 100 Mm NaCl. The radioactivity on the filters was counted with a LKB gamma counter.

2. CCK Receptor Binding (Brain)

CCK-8 sulphated was radiolabelled and the binding was performed according to the description for the pancreas method with minor modifications.

Male Hartley guinea pigs (300–500 g) were sacrificed by decapitation and the cortex was removed and homogenized in 25 mL ice-cold 0.32 M sucrose. The homogenates were centrifuged at 1000 g for 10 minutes and the resulting supernatant was recentrifuged at 20,000 g for 20 minutes. The P$_2$ pellet was resuspended in binding assay buffer (20 mM HEPES, 5 mM MgCl$_2$, 0.25 mg/ml bacitracin, 1 mM EGTA pH 6.5 at 25° C.), using a Teflon (trademark) homogenizer (5 strokes at 500 rpm) to give a final concentration of 10 mg original wet weight /1.2 ml buffer. For the binding assay, 50 μl of buffer (for total binding) or unlabelled CCK-8 sulphated to give a final concentration of 1 μM (for non-specific binding) or the compounds of Formula I (for determination of inhibition of $^{125}$I-CCK-8 binding) and 50 μl of 500 pM $^{125}$I-CCK-8 (i.e. final concentration of 50 pM) were added to 400 μl of the membrane suspensions in microfuge tubes. All assays were run in duplicate. The reaction mixtures were incubated at 25° C. for 2 hours and then the reaction was terminated by rapid filtration (Brandell 24 well cell harvester) on Whatman GF/C filters with 3×5 ml washes of cold 100 mM NaCl. The radioactivity on the filters was counted with a LKB gamma counter.

In Vitro Results

Effects of the Compounds of Formula I on $^{125}$I-CCK-8 Receptor Binding

The preferred compounds of Formula I are those which produced dose-dependent inhibition of specific $^{125}$I-CCK-8 binding as defined as the difference between total and non-specific (i.e. in the presence of 1 μM CCK) binding.

Drug displacement studies were performed with at least 10 concentrations of compounds of Formula I and the IC$_{50}$ values were determined by regression analysis IC$_{50}$ refers to the concentration of the compound required to inhibit 50% of specific binding of $^{125}$I-CCK-8.

The data in Table I were obtained for compounds of Formula I.

TABLE I

| CCK RECEPTOR BINDING RESULTS | | |
|---|---|---|
| | $IC_{50}$ (nM) | |
| Compound of Ex # | $^{125}$I-CCK Pancreas | $^{125}$I-CCK Brain |
| 1 | 500 | 0.123 |
| 2 | 110 | 5.98 |

We claim:

1. A compound of formula (I):

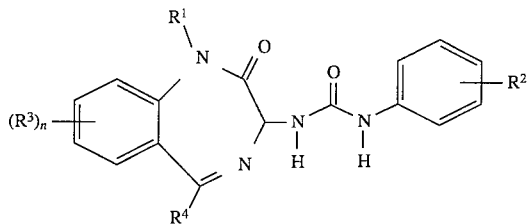

wherein:

$R^1$ represents H, $(CH_2)_q$imidazolyl, $(CH_2)_q$tetrazolyl, $(CH_2)_q$triazolyl, (where q is 1, 2 or 3); $C_{1-6}$alkyl optionally substituted by one or more groups selected from halo, hydroxy and $NR^6R^7$ (where $R^6$ and $R^7$ each independently represents H or $C_{1-4}$alkyl, or $R^6$ and $R^7$ together form a chain $(CH_2)_p$ where p is 4 or 5); $C_{3-7}$cycloalkyl; cyclopropylmethyl; $CH_2CO_2R^5$ (where $R^5$ is $C_{1-4}$alkyl), $CH_2CONR^6R^7$ or $CH_2CH(OH)$—W—$(CH_2)_2NR^6R^7$ where W is S or NH and $R^6$ and $R^7$ are as previously defined;

$R^2$ represents a group

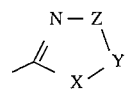

wherein:

X represents O, S or $NR^8$ where $R^8$ represents H or $C_{1-4}$alkyl;

one of Z and Y is C=O and the other is O, S or $NR^9$, where $R^9$ represents H or $C_{1-4}$alkyl;

$R^3$ represents $C_{1-6}$alkyl, or halo;

$R^4$ represents $C_{3-7}$cycloalkyl; and n is 0, 1, or 2;

or a pharmaceutically salt thereof.

2. A compound as claimed in claim 1 selected from:

N-[3(R)-5-cyclohexyl-2,3-dihydro-1-methyl-2-oxo-1H-1,4-benzodiazepin-3-yl]N'-[3-(5-oxo-4H-1,2,4-oxadiazolin-3-yl)phenyl]urea;

N-[3(R,S)-5-cyclobutyl-2,3-dihydro-1-methyl-2-oxo-1H-1,4-benzodiazepin-3-yl]N'-[3-(5-oxo-4H-1,2,4-oxadiazolin-3-yl)phenyl]urea;

N-[3(R,S)-5-cyclohexyl-2,3-dihydro-1-methyl-2-oxo-1H-1,4-benzodiazepin-3-yl]N'-[3-(5-oxo-4H-1,2,4-oxadiazolin-3-yl)phenyl]urea; and pharmaceutically acceptable salts thereof.

3. A compound as claimed in claim 1 wherein $R^1$ is $C_{1-6}$alkyl.

4. A compound as claimed in claim 1 wherein $R^2$ is oxadiazolinone.

* * * * *